United States Patent
Kumamoto et al.

(10) Patent No.: US 6,974,881 B2
(45) Date of Patent: Dec. 13, 2005

(54) PRODUCTION METHOD OF 4,6-DIAMINORESORCIN

(75) Inventors: Yukihiro Kumamoto, Fukuoka (JP); Masahiko Kusumoto, Fukuoka (JP); Hisato Itou, Kanagawa (JP); Hideki Mizuta, Fukuoka (JP); Masazumi Takaoka, Fukuoka (JP)

(73) Assignee: Mitsui Chemicals, Inc., Tokyo (JP)

( * ) Notice: Subject to any disclaimer, the term of this patent is extended or adjusted under 35 U.S.C. 154(b) by 741 days.

(21) Appl. No.: 10/058,415

(22) Filed: Jan. 30, 2002

(65) Prior Publication Data

US 2002/0107415 A1 Aug. 8, 2002

Related U.S. Application Data

(62) Division of application No. 09/556,814, filed on Apr. 21, 2000, now Pat. No. 6,359,180.

(30) Foreign Application Priority Data

| Apr. 30, 1999 | (JP) | 11-123328 |
| Jun. 7, 1999 | (JP) | 11-158850 |
| Jun. 28, 1999 | (JP) | 11-181093 |
| Jul. 28, 1999 | (JP) | 11-213013 |
| Oct. 12, 1999 | (JP) | 11-289055 |
| Oct. 21, 1999 | (JP) | 11-299465 |
| Nov. 18, 1999 | (JP) | 11-327647 |

(51) Int. Cl.$^7$ .......................... C07C 309/28
(52) U.S. Cl. ...................... 562/73
(58) Field of Search .............. 562/30, 45, 58, 562/73

(56) References Cited

U.S. PATENT DOCUMENTS

| 5,371,291 A | 12/1994 | Nader |
| 5,410,083 A | 4/1995 | Nader |

FOREIGN PATENT DOCUMENTS

FR 2 777 564 10/1999

OTHER PUBLICATIONS

CA:133:335633 abs of EP104864 Nov. 2000.*
Podstata, J. et al., "Sulfonations. X. The formation of sulfonated resorcinols and their azo coupling." Chemical Abstracts, vol. 68, No. 10, Mar. 4, 1968, Columbus, Ohio.

* cited by examiner

*Primary Examiner*—Jean F. Vollano
(74) *Attorney, Agent, or Firm*—Burns, Doane, Swecker & Mathis, LLP

(57) ABSTRACT

The present invention relates to a novel production method of 4,6-diaminoresorcin, and to 2-sulfonic acid-4,6-dinitroresorcin as its intermediate and salts thereof. The target compound is obtained by (R1) sulfonating resorcin (A) to obtain resorcin 2,4,6-trisulfonate (B), (R2) nitrating the compound (B) to obtain 2-sulfonic acid-4,6-dinitroresorcin (C), (R3) hydrolyzing the compound (C) to obtain 4,6-dinitroresorcin (D), and finally (R4) reducing the compound (D) to obtain 4,6-diaminoresorcin (E):

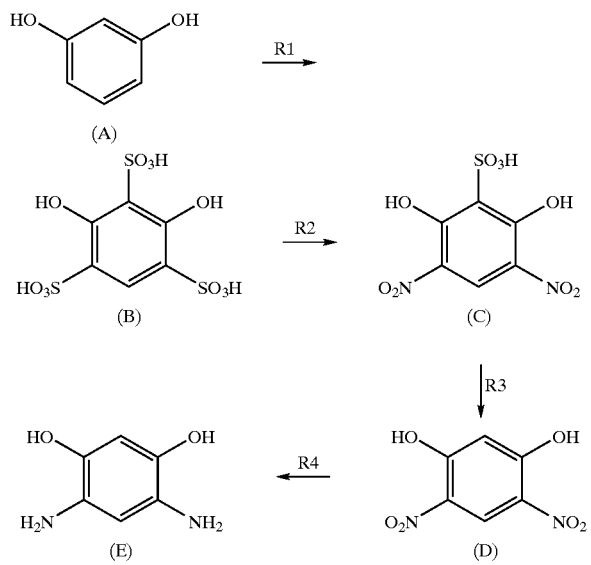

4 Claims, No Drawings

PRODUCTION METHOD OF 4,6-DIAMINORESORCIN

This application is a divisional of application No. 09/556,814, filed on Apr. 21, 2000, now U.S. Pat. No. 6, 359,180.

BACKGROUND OF THE INVENTION

1. Field of the Invention

The present invention relates to a novel production method of 4,6-diaminoresorcin which is a monomer for polybenzobisoxazole (PBO). More particularly, it relates to a production method of 4,6-diaminoresorcin in which resorcin is-used as a starting material, any step of forming a halogen-containing compound is not required and the production of by-products is inhibited. Furthermore, the present invention relates also to a novel intermediate useful for the synthesis of 4,6-diaminoresorcin and a production method of this intermediate.

A PBO fiber is superior to conventional fibers in terms of various properties such as strength, modulus of elasticity, heat resistance and chemical resistance, as disclosed in Japanese Patent Publication No. 501452/1986, so that it is expected to apply this kind of fiber to various uses including structural materials and thermal insulating materials as a super fiber which is superior to aramid, and hence the fiber is considered to be an industrially extremely useful resin. 4,6-Diaminoresorcin is a monomer for the PBO, and therefore, it is important as a raw material for the PBO.

2. Description of the Related Art

A PBO is a polymer represented by the following general structural formula (c) and can be obtained through a condensation reaction between a compound (a) and a compound (b) as represented by the following reaction formula:

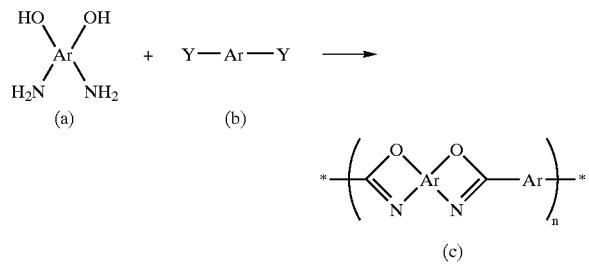

wherein Ar is an aromatic group; and Y is a functional group having an electron-deficient carbon such as a carboxyl group, a carboxylic acid halide group, a haloalkyl group or a nitrile group.

The thus obtained polybenzobisoxazole is used as fibers, films and the like, but its physical properties such as strength and modulus of elasticity are greatly influenced by a polymerization degree of the polymer. It is known that in a polycondensation reaction, a maximum polymer viscosity is generally obtained when a feed ratio of the monomers is 1:1, and the polymer viscosity rapidly decreases as the feed ratio of the monomers deviates from a ratio of 1:1. That is, to attain a satisfactory sufficient polymerization degree, it is necessary to strictly control the feed ratio of the monomers.

However, in the case that the monomers contain impurities in large quantities, it is difficult to control this feed ratio of the monomers. Particularly, when the monomers contain even small amounts of monoamine and triamines which act as polymerization terminators, the deterioration of the polymerization degree is caused. Therefore, there have been desired the high-purity monomers containing neither the monoamine nor the triamines.

As a monomer (a) for the PBO, 4,6-diaminoresorcin is known, and several synthesis methods for this compound have been reported.

A conventional production method of 4,6-diaminoresorcin comprises synthesizing dinitroresorcin as a precursor by a method in which resorcin is acetylated and then nitrated (Ber. Dtsch. Chem. Ges., 16, 552, 1883), a method in which 1,3-bis(alkyl carbonate)benzene is nitrated (Japanese Patent Application Laid-Open No. 136/1990) or another method, and then reducing the thus synthesized dinitroresorcin.

However, the operation of this conventional method is complicated and a manufacturing cost increases, because protecting groups are introduced for the hydroxy groups of resorcin, and from an industrial viewpoint, the above method has a problem that the protecting groups eliminated in a hydrolysis step become an unrecoverable by-product, and a problem that a trinitro compound is produced in the nitration step and a triamino compound is produced in the reduction step, and they disturb the polymerization in the synthesis of the PBO.

Furthermore, several methods using no protecting groups have been proposed in which a halobenzene is used as a raw material, and there are known, for example, a method in which a trichlorobenzene is nitrated (Japanese Patent Application Laid-Open No. 500743/1990) and a method in which a dihalobenzene is nitrated and then hydrolyzed with an alkali (Japanese Patent Application Laid-Open Nos. 238561/1989, 233127/1995, 316102/1995 and 73417/1996).

In these methods, however, since 4,6-dinitroresorcin is unstable under the alkali conditions in the hydrolysis step, the operation of these methods is apt to be complicated in order to avoid the decomposition of produced 4,6-dinitroresorcin. Furthermore, trichlorobenzene and its nitrated compound have a problem that they are strongly poisonous and cause an irritation on skin. Therefore, it is not preferable in consideration of the safety of an operator to pass through the production of a halogen-containing compound such as the halobenzene and its nitrated compound.

In addition, another method which comprises subjecting an aniline to diazotization and diazo-coupling the thus diazotized compound to resorcin, followed by hydrocracking is disclosed in Japanese Patent Application Laid-Open Nos. 242604/1995 and 124575/1997. In this method, however, aniline produced by the hydrocracking might be mixed with the product, and might disturb the polymerization in the synthesis of the PBO.

SUMMARY OF THE INVENTION

It is an object of the present invention to provide a novel production method of 4,6-diaminoresorcin in which any step of forming a halogen-containing compound is not required and the production of by-products is inhibited.

It is another object of the present invention to provide a-production method of 4,6-dinitroresorcin, as a precursor of 4,6-diaminoresorcin, via the production of a novel intermediate.

It is still another object of the present invention to provide a production method of a high-molecular-weight PBO by the use of high-purity 4,6-diaminoresorcin obtained by these methods.

The present inventors have made intensive studies to solve the above problems, and found that 4,6-diaminoresorcin can be obtained at a high yield by sulfonating resorcin to form resorcin 2,4,6-trisulfonate, nitrating resorcin 2,4,6-trisulfonate to obtain 2-sulfonic acid-4,6- dinitroresorcin with a high position selectivity, hydrolyzing this compound to form 4,6-dinitroresorcin, and then reducing the same. In consequence, the present invention has been attained.

Furthermore, the present inventors have found that a high-molecular-weight PBO can be obtained by hydrolyzing 2-sulfonic acid-4,6-dinitroresorcin to obtain 4,6-dinitroresorcin containing neither isomers nor trinitro compounds, reducing this compound to obtain high-purity 4,6-diaminoresorcin, and then polymerizing the same. Thus, the present invention has been achieved.

That is, the present invention includes the following aspects.

1. A production method of resorcin 2,4,6-trisulfonate which comprises the step of bringing resorcin into contact with a sulfonating agent.

2. The production method of resorcin 2,4,6-trisulfonate according to the above (1), wherein fuming sulfuric acid is used as the sulfonating agent.

3. The production method of resorcin 2,4,6-trisulfonate according to the above (2), wherein fuming sulfuric acid to be used contains 3 mols or more of free $SO_3$ per mol of resorcin.

4. A production method of 2-sulfonic acid-4,6-dinitroresorcin which comprises the step of nitrating resorcin 2,4,6-trisulfonate.

5. The production method of 2-sulfonic acid-4,6-dinitroresorcin according to the above (4), wherein the nitration is carried out in sulfuric acid or a fuming sulfuric acid solvent.

6. A production method of 2-sulfonic acid-4,6-dinitroresorcin which comprises the following steps:
   (1) a first step of producing resorcin 2,4,6-trisulfonate by bringing resorcin into contact with a sulfonating agent, and
   (2) a second step of producing 2-sulfonic acid-4,6-dinitroresorcin by bringing resorcin 2,4,6-trisulfonate into contact with a nitrating agent.

7. A production method of 4,6-dinitroresorcin which comprises the step of hydrolyzing 2-sulfonic acid-4,6-dinitroresorcin.

8. The production method of 4,6-dinitroresorcin according to the above (7), wherein the hydrolysis is carried out in water or an aqueous mineral acid solution.

9. The production method of 4,6-dinitroresorcin according to the above (8), wherein sulfuric acid is used as the mineral acid.

10. A production method of 4,6-dinitroresorcin which comprises the following steps:
    (1) a first step of producing resorcin 2,4,6-trisulfonate by bringing resorcin into contact with a sulfonating agent,
    (2) a second step of producing 2-sulfonic acid-4,6-dinitroresorcin by bringing resorcin 2,4,6-trisulfonate into contact with a nitrating agent, and
    (3) a third step of producing 4,6-dinitroresorcin by hydrolyzing 2-sulfonic acid-4,6-dinitroresorcin.

11. A production method of 4,6-diaminoresorcin which comprises the following steps:
    (1) a first step of producing resorcin 2,4,6-trisulfonate by bringing resorcin into contact with a sulfonating agent,
    (2) a second step of producing 2-sulfonic acid-4,6-dinitroresorcin by bringing resorcin 2,4,6-trisulfonate into contact with a nitrating agent,
    (3) a third step of producing 4,6-dinitroresorcin by hydrolyzing 2-sulfonic acid-4,6-dinitroresorcin, and
    (4) a fourth step of producing 4,6-diaminoresorcin by reducing 4,6-dinitroresorcin.

12. A production method of polybenzobisoxazole which comprises the steps of hydrolyzing 2-sulfonic acid-4,6-dinitroresorcin, followed by reducing to obtain 4,6-diaminoresorcin, and then reacting the thus obtained 4,6-diaminoresorcin with aromatic dicarboxylic acid.

13. 2-Sulfonic acid-4,6-dinitroresorcin represented by the following formula and salts thereof:

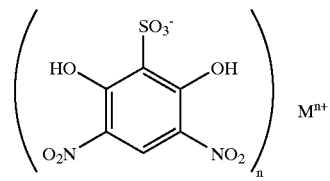

wherein M is hydrogen, an alkali metal or an alkaline earth metal, and n is 1 or 2.

14. A production method of 4,6-diaminoresorcin which comprises:
    (1) a first step of producing 4,6-dinitroresorcin by hydrolyzing 2-sulfonic acid-4,6-dinitroresorcin, and
    (2) a second step of producing 4,6-diaminoresorcin by reducing 4,6-dinitroresorcin.

15. The production method of 4,6-diaminoresorcin according to the above (14), wherein 2-sulfonic acid-4,6-dinitroresorcin is obtained by the following steps:
    (1) a first step of producing resorcin 2,4,6-trisulfonate by bringing resorcin into contact with a sulfonating agent, and
    (2) a second step of producing 2-sulfonic acid-4,6-dinitroresorcin by bringing resorcin 2,4,6-trisulfonate into contact with a nitrating agent.

16. The production method of 4,6-diaminoresorcin according to the above (14), wherein in the second step, 4,6-dinitroresorcin is reduced in an aqueous mineral acid solution.

17. The production method of 4,6-diaminoresorcin according to the above (16), wherein hydrochloric acid is used as the mineral acid.

18. The production method of 4,6-diaminoresorcin according to the above (14) which comprises the steps of dissolving or suspending 4,6-dinitroresorcin in a solvent, adjusting the pH of the suspension in a range of 4 to 5 to obtain 4,6-dinitroresorcin, and then reducing the thus obtained 4,6-dinitroresorcin.

DETAILED DESCRIPTION OF THE PREFERRED EMBODIMENTS

A production method of 4,6-diaminoresorcin of the present invention can be accomplished via the following intermediate compounds.

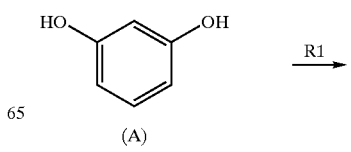

(A)

-continued

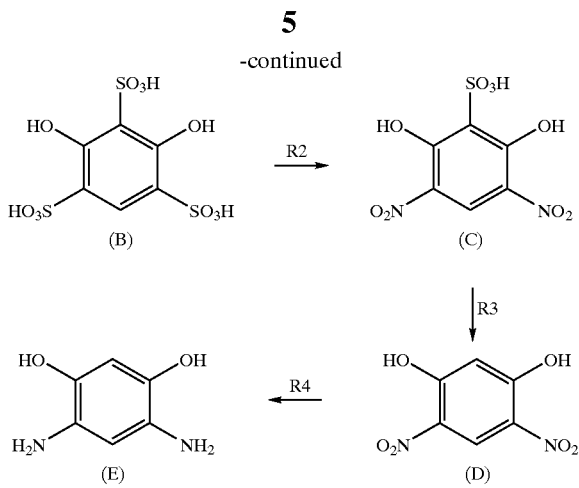

First, resorcin (i.e., 1,3-benzenediol) (A) as a raw material is brought into contact with a sulfonating agent (reaction R1) to obtain resorcin 2,4,6-trisulfonate (B). Successively, sulfonic groups at positions 4 and 6 are selectively nitrated (reaction R2) to obtain 2-sulfonic acid-4,6-dinitroresorcin (C), which is then hydrolyzed (reaction R3) to obtain 4,6-dinitroresorcin (D). Finally, 4,6-dinitroresorcin (D) is reduced (reaction R4) to obtain desired 4,6-diaminoresorcin (E).

To produce resorcin 2,4,6-trisulfonate, as described in Berichite, 10, 182, there is known a method in which a disulfonic acid resorcin is heated at 200° C. in fuming sulfuric acid. However, in the case that the thus formed disulfonic acid resorcin is isolated and then used in the subsequent step, a process becomes complicated and the serious decrease of yield occurs. Thus, the above method has been unsuitable for industrial practice.

Next, each of the reaction steps R1 to R4 will be described in detail hereinafter.

In the first reaction step R1, a sulfonating agent can be used that sulfonates resorcin (A) to produce resorcin 2,4,6-trisulfonate (B). Illustrative examples of the sulfonating agent include concentrated sulfuric acid, fuming sulfuric acid and sulfur trioxide. The reaction may be carried out using an appropriate solvent. However, it is industrially advantageous that the reaction is carried out in excess concentrated sulfuric acid or fuming sulfuric acid without using a solvent. To avoid desulfonation caused by hydrolysis, concentrated sulfuric acid or fuming sulfuric acid is preferably used at a concentration of 80 to 100% by weight, more preferably 95% by weight or more. Above all, the use of fuming sulfuric acid is most preferable.

According to the investigation of the present inventors, the selectivity of resorcin 2,4,6-trisulfonate depends largely on the concentration of $SO_3$ in sulfuric acid. As the $SO_3$ concentration in sulfuric acid decreases, the selectivity of resorcin 2,4,6-trisulfonate decreases. For example, even if 95 wt % sulfuric acid ($SO_3$ concentration=77.6%) is used, the preparation of resorcin 2,4,6-trisulfonate is possible, but it has been confirmed that in the case that 95 wt % sulfuric acid ($SO_3$ concentration=77.6%) is used, the selectivity of resorcin 2,4,6-trisulfonate is in a range of about 12 to 17 mol %, and remaining 83 to 88 mol % thereof is resorcin 4,6-disulfonate. This fact can be considered to be due to the decrease of the sulfuric acid concentration by water produced during the reaction. To attain such a yield as can be industrially satisfied, it is desirable that the $SO_3$ concentration in sulfuric acid at the completion of the reaction is 81.6% or more, i.e., the sulfuric acid concentration is about 100% or sulfuric acid contains an excessive amount of free $SO_3$. To maintain such a state, the sulfonation should be carried out by using fuming sulfuric acid containing 3 mols or more of free $SO_3$ per mol of resorcin.

The amount of the sulfonating agent to be used is not particularly limited, as long as it satisfies the above $SO_3$ concentration. It is, however, preferably 5 to 50 times more by weight than resorcin in view of volumetric efficiency and efficient agitation.

To bring resorcin into contact with the sulfonating agent, one of them may be added to the other or vice versa.

As for a reaction temperature, the reaction may be carried out within any temperature range in which the desired product can be obtained. However, a temperature range of from about 0 to about 200° C. is preferable. To avoid the installation of large cooling facilities which is required for heat generation at the time of the sulfonation, the reaction temperature is desirably 20° C. or higher. To prevent an undesirable side reaction, the reaction temperature is desirably 150° C. or lower.

Resorcin 2,4,6-trisulfonate can be isolated from a reaction mass by adding dropwise the reaction mass to an aqueous solution of an inorganic salt such as sodium sulfate to cause salting-out, followed by filtering and drying.

Next, reference will be made to the reaction step R2 in which 2-sulfonic acid-4,6-dinitroresorcin (C) is obtained from resorcin 2,4,6-trisulfonate (B). The reaction step R2 is a nitration step, in which a known nitrating agent capable of producing the desired compound can be used. Illustrative examples of the nitrating agent include nitric acid, fuming nitric acid, and nitrates such as sodium nitrate and potassium nitrate. The nitration may be carried out after the isolation of resorcin 2,4,6-trisulfonate from the sulfonated reaction mass as described above, but it is industrially advantageous that the nitration is carried out in a one-pot manner by adding the nitrating agent to the sulfonated reaction mass (in this case, the nitration is carried out in sulfuric acid or a fuming sulfuric acid solvent). The amount of the nitrating agent to be used is in a range of about 1 to 10 mols per mol of resorcin (A) as a starting material, and in order to sufficiently promote the reaction and to inhibit the excessive nitration, it is preferably in a range of about 2 to 4 mols per mol of resorcin (A).

The reaction step R2 can also be carried out within any temperature range in which the desired product can be obtained. However, when the reaction temperature is too high, the reaction proceeds quickly, whereby the undesirable side reaction may occur on occasion. Therefore, the reaction is usually carried out while the reaction temperature is controlled by cooling. The reaction temperature is preferably in a range of about 0 to 80° C., more preferably about 0 to 50° C.

To isolate desired 2-sulfonic acid-4,6-dinitroresorcin (C) from the reaction mass after the completion of the reaction, the reaction mass is first neutralized with an alkali to form an alkali metal salt or an alkaline earth metal salt, which is then subjected to salting-out to thereby deposit the salt, so that the desired salt is obtained as a mixture with an alkali metal salt or an alkaline earth metal salt of sulfuric acid. In succesion, the mixture is added to, for example, a mixed solution containing water and ethanol in a ratio of 2:8, and the resultant solution is then heated at 50 to 80° C. to dissolve the desired compound. Afterward, the inorganic salt is removed by filtration under heating. The resultant filtrate is cooled to deposit yellow crystals, which are then filtered to thereby obtain an alkali metal salt or an alkaline earth metal salt of 2-sulfonic acid-4,6-dinitroresorcin (C). Alternatively, the solvent may be removed from the filtrate to obtain the alkali metal salt or the alkaline earth metal salt of 2-sulfonic acid-4,6-dinitroresorcin (C). The alkali metal salt or the alkaline earth metal salt can be desalted by dissolving the salt in water, passing the solution through a column filled with a strongly acidic cation exchange resin, and removing water therefrom. In consequence, 2-sulfonic acid-4,6-dinitroresorcin (C) is obtained.

Next, reference will be made to the reaction step R3 in which 2-sulfonic acid-4,6-dinitroresorcin (C) is hydrolyzed to obtain 4,6-dinitroresorcin (D).

The hydrolysis is carried out in water or an aqueous solution containing an acid or an alkali as a catalyst. However, it is preferably carried out in water or the acid-containing aqueous solution, more preferably in a mineral acid-containing aqueous solution, because there is a fear that 4,6-dinitroresorcin (D) after the hydrolysis may bring about a further decomposition reaction in the alkali aqueous solution having a high concentration. Examples of the mineral acid which can be used herein include sulfuric acid, hydrochloric acid and phosphoric acid. The mineral acid is preferably sufficiently diluted with water, or a sulfuric acid coupling agent may be added thereto in order to avoid the recombination of the separated sulfonic group. In the hydrolysis step R3, the concentration of the mineral acid is preferably in a range of 5 to 90% by weight, and in order to maintain a sufficient hydrolysis rate and to obtain a sufficient yield, it is desirably 10% by weight or more. The amount of the aqueous mineral acid solution to be used is not particularly limited, but it is preferably about 2 to 50 times by weight more than 2-sulfonic acid-4,6-dinitroresorcin (C) in view of agitation efficiency and volumetric efficiency. The reaction temperature is preferably in a range of from 50° C. to reflux temperature or so.

This hydrolysis step R3 may be carried out after 2-sulfonic acid-4,6-dinitroresorcin (C) has been isolated, or alternatively it may be carried out without isolating 2-sulfonic acid-4,6-dinitroresorcin (C) from the reaction mass in the nitration step R2.

When the hydrolysis is directly carried out without isolating 2-sulfonic acid-4,6-dinitroresorcin (C), the reaction mass in the nitration step R2 is diluted so as to become the aqueous mineral acid solution which meets predetermined conditions. Furthermore, when 2-sulfonic acid-4,6-dinitroresorcin is isolated as the alkali metal salt or the alkaline earth metal salt, the salt may be directly used as it is in the hydrolysis step. In addition, the salt may be used in the form of a mixture with an alkali sulfate.

As the hydrolysis reaction proceeds, crystals of 4,6-dinitroresorcin (D) are gradually deposited. Therefore, these crystals are filtered after the completion of the reaction to obtain the desired product. The thus obtained 4,6-dinitroresorcin (D) may be purified as required prior to its use. The compound 4,6-dinitroresorcin (D) may be purified by subjecting it to sludging in or recrystallization from a solvent such as ethanol. However, it is preferable for the purpose of preventing the deterioration of a catalytic activity in the reduction step to dissolve or suspend 4,6-dinitroresorcin (D) in a solvent such that the resulting solution has a pH of 4 to 5. Concretely, any of the following procedures can be taken.

(1) An alkali is added to a solution or slurry in which 4,6-dinitroresorcin is dissolved or suspended in a solvent, thereby adjusting the pH in a range of 4 to 5.

(2) 4,6-Dinitroresorcin is dissolved in a two-layer mixed solvent of water and a hydrophobic solvent, and an alkali is then added to the solution, thereby adjusting the pH in a range of 4 to 5.

(3) 4,6-Dinitroresorcin, which is in the form of an alkali salt, is dissolved in water, and an acid is then added to the solution, thereby adjusting the pH in a range of 4 to 5.

Examples of a hydrophilic solvent which is one type of the solvent to be used include water, methanol, ethanol, n-propanol, iso-propanol, DMI (1,3-dimethyl-2-imidazolidinone) and DMF (N,N-dimethylformamide). Examples of a hydrophobic solvent which is the other type of the solvent to be used include ethyl acetate, 1,3-dimethoxybenzene, phenetole and anisole. The amount of the solvent depends on the kind of solvent to be used, but it is in a range of 1 to 100 times more than that of 4,6-dinitroresorcin. The above alkali is not particularly limited, but its examples include potassium hydroxide, sodium hydroxide, potassium carbonate and sodium carbonate. The above acid is not particularly limited, but its examples include mineral acid such as hydrochloric acid and sulfuric acid. A temperature at the pH adjustment depends on the kind of solvent to be used, but it is preferably in a range of 10 to 80°C.

The isolation of purified 4,6-dinitroresorcin, in the case that the pH adjustment is made in the slurry state, is carried out by filtrating the slurry as it is, washing the collected substance with the used solvent, and further washing it with water. In the case that the pH adjustment is made in the two-layer heterogeneous state, the isolation is carried out by allowing the obtained solution to stand for separation, washing the separated organic phase with water, cooling it for crystallization, and then filtering the resultant crystals. In the case that 4,6-Dinitroresorcin in the form of the alkali salt is dissolved and the acid is then added, the isolation is carried out merely by filtrating the obtained mixture as it is, and then washing it with water.

Finally, reference will be made to the reduction step R4 in which 4,6-diaminoresorcin (E) is obtained from 4,6-dinitroresorcin (D).

In this step, any reduction technique may be used as long as the desired product is obtained. However, a catalytic reduction is usually carried out in the presence of a noble metal catalyst. The noble metal catalyst to be used herein is a platinum group metal such as palladium, platinum, rhodium or ruthenium which is carried on a proper carrier, and it is preferable to use palladium or platinum carried on carbon.

The amount of the catalyst to be used is in a range of 0.1 to 10% by weight, preferably 0.5 to 5% by weight, based on 4,6-dinitroresorcin (D). A reaction temperature is in a range of 20 to 100° C., and a hydrogen pressure is in a range of 0.1 to 10 MPa.

The solvent usable in the reaction is water, an organic solvent, an organic acid, or a mixture of water and a mineral acid. Examples of the usable mineral acid include hydrochloric acid, phosphoric acid and sulfuric acid. Above all, the employment of hydrochloric acid is preferable, because a hydrochloride of 4,6-diaminoresorcin is formed simultaneously with the reduction of 4,6-dinitroresorcin and this hydrochloride is dissolved in water to form a homogeneous solution which is easy to handle. Examples of the organic solvent include aromatic hydrocarbons such as benzene and toluene, and alcohols such as methanol and ethanol. Examples of the organic acid include acetic acid and propionic acid.

The formed 4,6-diaminoresorcin (E) is converted into a mineral acid salt to avoid oxidation/decomposition, and this salt is then isolated by a known technique such as precipitation or filtration. More specifically, for example, the reaction mass is added to a diluted aqueous hydrochloric acid solution containing stannous chloride to dissolve 4,6-diaminoresorcin hydrochloride. In succession, the resulting solution is filtered to remove the catalyst, and then the solvent is distilled off under reduced pressure. Alternatively, the filtrated solution is mixed with concentrated hydrochloric acid to deposit crystals, followed by filtration. When the aqueous hydrochloric acid solution is used as the solvent, 4,6-diaminoresorcin hydrochloride is already formed in the reduction reaction mass, and hence the steps of the salt-forming and the dissolving are not necessary. When phosphoric acid or sulfuric acid is used as the mineral acid and the 4,6-diaminoresorcin mineral acid salt is deposited, the salt is dissolved in the form of 4,6-diaminoresorcin hydrochloride by salt-exchanging, and crystals are then deposited in the similar manner as above.

An obtained 4,6-diaminoresorcin dimineral acid salt can be further purified by a technique such as recrystallization. concretely, for example, after crude 4,6-diaminoresorcin dimineral acid salt is dissolved in water including stannous chloride, activated carbon is added thereto, followed by treatment. Next, the activated carbon is removed by filtration, and concentrated hydrochloric acid is then added thereto for crystallization.

In order to obtain a PBO by the use of the thus obtained 4,6-diaminoresorcin (E), a known polymerization method can be employed. For example, the PBO can be obtained by dissolving the 4,6-diaminoresorcin dimineral acid salt in polyphosphoric acid, heating the resulting solution under reduced pressure to remove hydrochloric acid, adding a required amount of diphosphorus pentoxide, further adding aromatic dicarboxylic acid in a nearly equimolar amount to 4,6-diaminoresorcin, and then stirring the mixture under heat. Examples of the usable aromatic dicarboxylic acid include terephthalic acid, isophthalic acid, 4,4'-bis(benzoic acid), 4,4'-oxybis(benzoic acid) and 2,6-naphthalene dicarboxylic acid.

The present invention will be described in more detail with reference to the following examples, by which the present invention is not limited.

EXAMPLE 1

Sulfonation Step R1

100 g of 30 wt % fuming sulfuric acid ($SO_3$ concentration=87.1%, the amount of free $SO_3$=3.75 mols per mol of resorcin) were cooled with ice, 11.0 g (0.1 mol) of resorcin were slowly added thereto. Afterward, the mixture was heated to 90° C. to give a dark-red homogeneous solution of a reaction mass. According to the analysis of liquid chromatography (hereinafter abbreviated to "HPLC"), any peaks of resorcin and resorcin 4,6-disulfonate were not confirmed, and the production ratio of resorcin 2,4,6-trisulfonate was 99.8 mol %.

Conditions for HPLC Analysis

Column: YMC-312A (ODS)
Mobile phase: Acetonitrile:water:PIC=1000:2000:10
PIC=Tetrabutyl ammonium hydroxide
Flow rate: 1 ml/min
Detection wavelength: 254 nm
Thermostat layer: 40° C.

EXAMPLE 2

Sulfonation Step R1

100 g of 24 wt % fuming sulfuric acid ($SO_3$ concentration=86.0%, the amount of free $SO_3$=3 mols per mol of resorcin) were cooled with ice, and 11.0 g (0.1 mol) of resorcin were slowly added thereto. Afterward, the mixture was heated to 50° C. to give a dark-red homogeneous solution of a reaction mass. According to the analysis of HPLC, the production ratio of resorcin 4,6-disulfonate was 0.6 mol %, and that of resorcin 2,4,6-trisulfonate was 99.3 mol %.

EXAMPLE 3

Sulfonation step R1

100 g of 16 wt % fuming sulfuric acid ($SO_3$ concentration=84.6%, the amount of free $S_3$=2 mols per mol of resorcin) were cooled with ice, and 11.0 g (0.1 mol) of resorcin were slowly added thereto. Afterward, the mixture was heated to 90° C., so that a reaction mass was obtained in the state of an orange-colored viscous slurry containing a slight amount of a solid. According to the analysis of HPLC, the production ratio of resorcin 4,6-disulfonate was 9.5 mol %, and that of resorcin 2,4,6-trisulfonate was 90.2 mol %. The reaction mass was further heated to 130° C. to obtain a red homogeneous solution, but after reaction for 30 minutes, the production ratio of resorcin 4,6-disulfonate was 13 mol %, and that of resorcin 2,4,6-trisulfonate was 87 mol %.

EXAMPLE 4

Sulfonation step R1

100 g of 100 wt % sulfuric acid ($SO_3$ concentration=81.6%) were cooled with ice, and 11.0 g (0.1 mol) of resorcin were slowly added thereto. Afterward, the mixture was heated to 90° C., so that a reaction mass was obtained in the state of a light pink slurry. According to the analysis of HPLC, the production ratio of resorcin 4,6-disulfonate was 93 mol %, and that of resorcin 2,4,6-trisulfonate was 6.5 mol %. The reaction mass was further heated to 130° C., but no dissolution of crystals was observed, and the reaction mass remained in the form of the light pink slurry. After reaction for 60 minutes, the production ratio of resorcin 4,6-disulfonate was 79 mol %, and that of resorcin 2,4,6-trisulfonate was 21 mol %.

EXAMPLE 5

Sulfonation Step R1

100 g of 95 wt % sulfuric acid ($SO_3$ concentration=77.6%) were cooled with ice, and 11.0 g (0.1 mol) of resorcin was slowly added thereto. Afterward, the mixture was heated to 50° C., so that a reaction mass was obtained in the state of a white slurry. According to the analysis of HPLC, the production ratio of resorcin 4,6-disulfonate was 88 mol %, and that of resorcin 2,4,6-trisulfonate was 12 mol %.

EXAMPLE 6

Sulfonation Step R1

200 g of 95 wt % sulfuric acid ($SO_3$ concentration=77.6%) were cooled with ice, and 11.0 g (0.1 mol) of resorcin was slowly added thereto. Afterward, the mixture was heated to 50° C., so that a reaction mass was obtained in the state of a white slurry. According to the analysis of HPLC, the production ratio of resorcin 4,6-disulfonate was 83 mol %, and that of resorcin 2,4,6-trisulfonate was 17 mol %.

EXAMPLE 7

Nitration Step R2

In the same manner as in Example 1, 5.5 g (0.05 mol) of resorcin were added to 50 g of 30 wt % fuming sulfuric acid, and the resultant sulfonated mass was then cooled with ice. Afterward, 10.5 g (0.1 mol) of 60 wt % nitric acid were added dropwise thereto, so that heat was vigorously generated and the reaction mass became a yellow-brown slurry.

This nitrated mass was added to 100 g of ice, and 27.7 g of a 49% aqueous sodium hydroxide solution were then added dropwise thereto under ice cooling, so that yellow-white crystals were deposited to form a slurry. The slurry was filtered, and the resultant filter cake was then washed with 100 g of ethanol to obtain 9.44 g of a mixture of 2-sulfonic acid-4,6-dinitroresorcin sodium salt and sodium sulfate.

5.04 g of the above mixture were added to 200 g of a mixed solution of water and ethanol in a ratio of 20:80. After the mixture was sludged and filtered under heat at 80° C., the filtrate was cooled by allowing it to stand at room temperature, so that the deposition of crystals was observed. Next, the crystals were collected by filtration to obtain 1.07 g of yellow crystals of 2-sulfonic acid-4,6-dinitroresorcin sodium salt.

1.07 g of this compound were dissolved in 25 g of water, and the resultant solution was passed through a column filled with 20 ml of an ion exchange resin (MD-S1368) and then washed with 30 g of water. This solution was evaporated by an evaporator, dried under nitrogen, washed with ethanol, and then filtered to obtain 130 mg of crystals of 2-sulfonic acid-4,6-dinitroresorcin.

The $^{13}$C-NMR spectrum of 2-sulfonic acid-4,6-dinitroresorcin synthesized in this example showed the following absorptions, and these absorptions were ascribed to carbons a to d in the following structural formula, respectively.

$\delta$ = 119.4 ppm   a (aromatic carbon substituted by $NO_2$)
$\delta$ = 125.2 ppm   b (aromatic carbon substituted by $SO_3H$)
$\delta$ = 128.9 ppm   c (aromatic carbon to which hydrogen was bonded)
$\delta$ = 155.0 ppm   d (aromatic carbon substituted by OH)

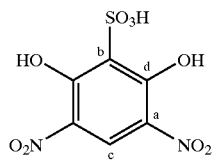

Furthermore, according to the measurement of an infrared-absorbing spectrum, the following distinctive absorption bands were observed.

| | |
|---|---|
| 1588 cm$^{-1}$ | $NO_2$ (absorbing band due to asymmetric stretching vibration) |
| 1363 cm$^{-1}$ | $NO_2$ (absorbing band due to symmetric stretching vibration) |
| 1332 cm$^{-1}$ | $SO_2$ (absorbing band due to asymmetric stretching vibration) |
| 1154 cm$^{-1}$ | $SO_2$ (absorbing band due to symmetric stretching vibration) |

EXAMPLE 8

Nitration Step R2

4.12 g of 9.44 g of a mixture of 2-sulfonic acid-4,6-dinitroresorcin sodium salt obtained in Example 7 and sodium sulfate were added to 100 g of a mixed solution of water and ethanol in a ratio of 20:80. After the mixture was sludged and filtered under heat at 80° C., the filtrate was cooled by allowing it to stand at room temperature, so that the deposition of crystals was observed. The crystals were collected by filtration and then air-dried under nitrogen to obtain 1.18 g of yellow crystals of 2-sulfonic acid-4,6-dinitroresorcin sodium salt.

The $^{13}$C-NMR spectrum of 2-sulfonic acid-4,6-dinitroresorcin sodium salt synthesized in this example showed the following absorptions, and these absorptions were ascribed to carbons a to d in the following structural formula, respectively.

$\delta$ = 119.4 ppm   a (aromatic carbon substituted by $NO_2$)
$\delta$ = 125.2 ppm   b (aromatic carbon substituted by $SO_3H$)
$\delta$ = 128.9 ppm   c (aromatic carbon to which hydrogen was bonded)
$\delta$ = 155.0 ppm   d (aromatic carbon substituted by OH)

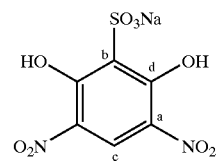

Furthermore, according to the measurement of an infrared-absorbing spectrum, the following distinctive absorption bands were observed.

| | |
|---|---|
| 1588 cm$^{-1}$ | $NO_2$ (absorbing band due to asymmetric stretching vibration) |
| 1363 cm$^{-1}$ | $NO_2$ (absorbing band due to symmetric stretching vibration) |
| 1332 cm$^{-1}$ | $SO_2$ (absorbing band due to asymmetric stretching vibration) |
| 1154 cm$^{-1}$ | $SO_2$ (absorbing band due to symmetric stretching vibration) |

Elementary Analysis Values (%) of $C_6H_3N_2O_9SNa$

| Element | C | H | N | S | Na |
|---|---|---|---|---|---|
| Calcd. | 23.86 | 1.00 | 9.27 | 10.59 | 7.61 |
| Found | 23.68 | 0.99 | 9.24 | 10.80 | 7.89 |

EXAMPLE 9

Hydrolysis Step R3

15.1 g (0.05 mol) of 2-sulfonic acid-4,6-dinitroresorcin sodium salt were added to 250 g of a 20 wt % aqueous sulfuric acid solution, and the resultant solution was then heated at 100° C. for 7 hours, during which the gradual deposition of crystals was observed. After the reaction mass was cooled to room temperature, it was collected by filtration to obtain 8.95 g of yellow-white crystals. The crystals were recrystallized from 500 g of ethanol, and then air-dried under nitrogen to obtain 7.6 g of purified 4,6-dinitroresorcin.

EXAMPLE 10

R1 to R3 in sequence 5.5 g (0.05 mol) of resorcin were slowly added to 50 g of 30% fuming sulfuric acid, and the reaction mass was then heated to 90° C. to thereby become a dark-red solution. The production of resorcin 2,4,6-trisulfonate was confirmed by HPLC analysis. The sulfonated mass was cooled with ice, and 10.5 g (0.1 mol) of 60% nitric acid was then added dropwise thereto, so that heat was vigorously generated and the reaction mass became a yellow-brown slurry.

The nitrated mass was added to 100 g of ice, and then heated to 100° C. to carry out hydrolysis, so that the gradual deposition of crystals was observed. The crystals were collected by filtration and air-dried under nitrogen to obtain 8.02 g (yield=80.3% based on resorcin) of 4,6-dinitroresorcin.

EXAMPLE 11

Steps R1 to R4

55 g (0.5 mol) of resorcin were slowly added to 500 g of 30 wt % fuming sulfuric acid, and the mixture was heated to 90° C., so that the reaction mass became a dark-red solution. The production of resorcin 2,4,6-trisulfonate was confirmed by HPLC analysis.

The sulfonated mass was cooled with ice, and 105 g (1.0 mol) of 60 wt % nitric acid was added dropwise thereto, so that heat was vigorously generated and the reaction mass became a yellow-brown slurry. This nitrated mass was added to 1,095 g of ice, and then heated to 100° C. to carry out hydrolysis, so that the gradual deposition of crystals was observed. The crystals were collected by filtration, sludged with 500 g of water, and then air-dried under nitrogen to obtain 81.2 g (yield=81.2%) of crude 4,6-dinitroresorcin.

30 g of crude 4,6-dinitroresorcin were recrystallized in 1,500 g of ethanol to obtain 24.1 g of purified 4,6-dinitroresorcin. Next, 4.0 g of this purified 4,6-dinitroresorcin were added to methanol, and 0.0396 g of 5% palladium carbon (a 50% wet product) was then added thereto, followed by hydrogenation at 60° C. under an average hydrogen pressure of 0.8 MPaG. The reaction mass was poured into a 5% aqueous hydrochloric acid solution containing 6,000 ppm of stannous chloride, and then filtered to remove the catalyst. Afterward, analysis was carried out by HPLC, and it was confirmed that desired 4,6-diaminoresorcin was produced in a yield of 96.2 mol %. The solvent was removed from the filtrate by an evaporator to obtain the crystals of crude 4,6-dinitroresorcin. The crystals were dissolved in 21.3 g of water containing 0.32 g of stannous chloride, and 0.2 g of activated carbon was added to the solution. Thereafter, the solution was stirred for 30 minutes and then filtered to remove the activated carbon. When 16.0 g of 36% hydrochloric acid were gradually added dropwise to the filtrate, the gradual deposition of crystals was observed. The crystals were collected by filtration and then dried at 50° C. under reduced pressure to obtain 3.03 g (yield=46.4%) of 4,6-diaminoresorcin dihydrochloride.

EXAMPLE 12

10 g of purified 4,6-dinitorresorcin obtained in Example 11 were added to 73.4 g of a 5.2% aqueous hydrochloric acid solution. To the solution was added 0.9 g of 2% platinum carbon (a 56% water-containing product), and hydrogenation was then carried out at 60° C. under a hydrogen pressure of 0.8 MPa. After the reaction mass was filtered to remove the catalyst, 0.75 g of activated carbon was added to the filtrate. Thereafter, the filtrate was stirred for 30 minutes and then filtered to remove the activated carbon. When 23 g of hydrogen chloride were added to the filtrate, the gradual deposition of crystals was observed. The crystals were collected by filtration and then dried under reduced pressure to obtain 10.2 g (yield=95.7%) of 4,6-diaminoresorcin dihydrochloride.

EXAMPLE 13

32 g (0.16 mol) of 4,6-dinitroresorcin produced in the same manner as in Example 10 were added to 1,440 g of ethyl acetate, and the mixture was then heated to 80° C. to become a homogeneous solution. Next, 200 g of hot water at 80° C. were added to the mixture, and a pH electrode was then immersed into the solution. Afterward, a 49% aqueous sodium hydroxide solution was added dropwise thereto to adjust a pH of the system to 4.3, and the solution was then stirred at the same temperature for one hour.

The stirring was terminated, and the solution-was then allowed to stand for one hour. Thereafter, water was discharged through the bottom of the flask. 200 g of hot water was-added to the remaining 4,6-dinitroresorcin ethyl acetate solution in the flask, followed by stirring at 80° C. for one hour. After the stirring was stopped, the solution was allowed to stand for one hour and the resultant liquid phases were then separated. This operation was further repeated twice.

The remaining 4,6-dinitroresorcin ethyl acetate solution in the flask was gradually cooled to 20° C. to deposit yellow crystals. This solution was suction-filtered, washed with hot water, and then dried at 30° C., thereby obtaining 20.8 g of 4,6-dinitroresorcin.

20 g of the thus obtained 4,6-dinitroresorcin, 0.4 g of 2% platinum carbon and 146.7 g of a 5.2% aqueous hydrochloric acid solution were placed in a 0.3-liter autoclave made of tantalum, and hydrogenation reaction was then carried out at a reaction temperature of 60° C. and a stirring speed of 1,000 rpm under a hydrogen pressure of 0.78 MPa. The reaction was completed in a reaction time of 95 minutes. Thereafter, the catalyst was filtered out, whereby a colorless transparent reaction solution was obtained. The reaction results in this case were such that the conversion rate of 4,6-dinitroresorcin was 100% and the yield of 4,6-diaminoresorcin dihydrochloride was 98%.

In succession, 35 g of hydrogen chloride were blown into the above reaction solution to deposit white crystals. This solution was filtered, washed with acetone, and then dried at 30° C. to obtain 20.4 g of white 4,6-diaminoresorcin dihydrochloride.

EXAMPLE 14

32 g of 4,6-dinitroresorcin produced in the same manner as in Example 10 were added to 128 g of methanol, and the resulting mixture was then heated to 50° C. To the obtained slurry solution was added a 49% aqueous sodium hydroxide solution to adjust the pH of the solution to 4.3. After stirred at the same temperature for one hour, the solution was cooled to 20° C. This treated solution was filtered, washed with methanol and then water, and dried at 30° C. to obtain 31.2 g of 4,6-dinitroresorcin. 20 g of the thus obtained 4,6-dinitroresorcin, 0.4 g of 2% platinum carbon and 146.7 g of a 5.2% aqueous hydrochloric acid solution were placed in a 0.3-liter autoclave made of tantalum, and hydrogenation reaction was then carried out at a reaction temperature of 60° C. and a stirring speed of 1,000 rpm under a hydrogen pressure of 0.78 MPa. The reaction was completed in a reaction time of 100 minutes. Thereafter, the catalyst was filtered out to obtain a reaction solution. The reaction results in this case were such that the conversion rate of 4,6-dinitroresorcin was 100% and the yield of 4,6-diaminoresorcin dihydrochloride was 97.5%.

EXAMPLE 15

50 g of 4,6-dinitroresorcin produced in the same manner as-in Example 10 were added to 570 g of water, and 40.8 g of a 49% aqueous sodium hydroxide solution were added to the mixture at a temperatures of 20 to 30° C. to prepare a homogeneous solution. A 36% aqueous hydrochloric acid solution was added dropwise to the above homogenous solution to adjust the pH of the solution to 4.3, so that the material became a slurry state. This slurry was filtered, washed with water, and then dried at 30° C. to obtain 49 g of 4,6-dinitroresorcin.

20 g of the thus obtained 4,6-dinitroresorcin, 0.4 g of 2% platinum carbon and 146.7 g of a 5.2% aqueous hydrochloric acid solution were placed in a 0.3-liter autoclave made of tantalum, and hydrogenation reaction was then carried out at a reaction temperature of 60° C. and a stirring speed of 1,000 rpm under a hydrogen pressure of 0.78 MPa. The reaction was completed in a reaction time of 100 minutes. Thereafter, the catalyst was filtered out to obtain a reaction solution. The reaction results in this case were such that the conversion rate of 4,6-dinitroresorcin was 100% and the yield of 4,6-diaminoresorcin dihydrochloride was 97.6%.

EXAMPLE 16

Steps R1 to R4 and polymerization of PBO)

110.0 g (1 mol) of resorcin were slowly added to 1,000 g of 30% fuming sulfuric acid, and the mixture was then heated up to 50° C., so that a reaction mass became a dark-red solution. According to HPLC analysis, the production of resorcin 2,4,6-trisulfonate was confirmed.

The sulfonated mass was cooled with ice, and 210 g (2 mol) of 60 wt % nitric acid were added dropwise thereto, so that heat was vigorously generated and the reaction mass became a yellow-brown slurry.

The nitrated mass was poured into 2,200 g of ice, followed by hydrolysis at 100° C. for 7 hours, so that the gradual deposition of crystals was observed. The solution was cooled to room temperature and then filtered, and the obtained crystals were washed with ethanol, filtered and air-dried under nitrogen to obtain 130.5 g (yield=65.2%) of 4,6-dinitroresorcin.

This 4,6-dinitroresorcin was placed in an autoclave, and 660 ml of methanol and 2.7 g of 5% Pd/C were further added to the autoclave. Here, hydrogenation reaction was carried out at 60° C. under a hydrogen pressure of 0.78 MPa. When the absorption of hydrogen was no longer observed, the reaction mass was cooled to room temperature, and then poured into 760 g of a 5% aqueous hydrochloric acid solution to dissolve the product therein. After the mixture was filtered to remove the catalyst, the solvent was removed therefrom by an evaporator to obtain 133.6 g (yield=62.7%) of crude 4,6-diaminoresorcin dihydrochloride.

This crude 4,6-diaminoresorcin dihydrochloride was dissolved-in 670 g of water containing 10 g of stannous chloride, and 11 g of activated carbon were added for a discoloration treatment. The mixture was filtered to remove the activated carbon, and 510 g of 36% hydrochloric acid were added dropwise to the filtrate to deposit crystals, which were then filtered out to obtain 106.6 g (yield=50.01%) of purified 4,6-diaminoresorcin dihydrochloride.

40% by weight of 85% $H_3P_4$ and 60 wt % of 115% polyphosphoric acid were mixed with each other to prepare a polyphosphoric acid solution (a PPA solution) containing 74.9% of $P_2O_5$. Then, 22.82 g (0.11 mol) of the above-described purified 4,6-diaminoresorcin dihydrochloride were added to 88.6 g of the PPA solution, and the solution was stirred and then heated at 50 to 80° C. for about 20 hours under reduced pressure to remove hydrochloric acid therefrom. To this mixture were added 17.96 g (0.11 mol) of terephthalic acid, and then 61.2 g of $P_2O_5$ were added thereto to adjust the content of $P_2O_5$ in the mixture to 87.2 wt %. This mixture was stirred at 100° C. for 15 hours under argon stream. Then, while the mixed solution was vigorously stirred, its temperature was elevated up to 178° C. within 40 minutes, and at this temperature, the solution was further stirred for 25 hours. Next, the temperature of the solution was elevated up to 185° C. within one hour, and at this temperature, the solution was allowed to react for 25 hours to obtain a reaction solution containing poly(p-phenylenebenzobisoxazole) (PBO). This reaction solution was precipitated in water, and fully washed with water to prepare a PBO powder from which the PPA was completely removed. The intrinsic viscosity of the obtained PBO was 25.2 dl/g (30° C., methanesulfonic acid).

What is claimed is:

1. 2-Sulfonic acid-4,6-dinitroresorcin represented by the following formula and salts thereof:

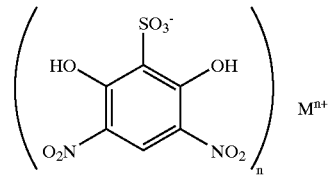

wherein M is hydrogen, an alkali metal or an alkaline earth metal, and n is 1 or 2.

2. A method for producing 2-sulfonic acid-4,6-dinitroresorcin which comprises the step of nitrating resorcin 2,4,6-trisulfonate.

3. The method for producing 2-sulfonic acid-4,6-dinitroresorcin according to claim 2, wherein the nitration is carried out in sulfuric acid or a fuming sulfuric acid solvent.

4. A method for producing 2-sulfonic acid-4,6-dinitroresorcin which comprises the following steps:

(1) a first step of producing resorcin 2,4,6-trisulfonate by bringing resorcin into contact with a sulfonating agent, and (2) a second step of producing 2-sulfonic acid-4,6-dinitroresorcin by bringing resorcin 2,4,6-trisulfonate into contact with a nitrating agent.

* * * * *